(12) United States Patent
Janda et al.

(10) Patent No.: US 10,722,278 B2
(45) Date of Patent: Jul. 28, 2020

(54) IMPLANTABLE BONE ADJUSTMENT DEVICES

(71) Applicant: Smith & Nephew, Inc., Memphis, TN (US)

(72) Inventors: Haden Janda, Cordova, TN (US); Gene Edward Austin, Bartlett, TN (US); Sied William Janna, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 16 days.

(21) Appl. No.: 16/142,269

(22) Filed: Sep. 26, 2018

(65) Prior Publication Data

US 2019/0105086 A1    Apr. 11, 2019

Related U.S. Application Data

(60) Provisional application No. 62/568,888, filed on Oct. 6, 2017.

(51) Int. Cl.
*A61B 17/72* (2006.01)
*A61B 17/00* (2006.01)

(52) U.S. Cl.
CPC ............... *A61B 17/7216* (2013.01); *A61B 2017/00398* (2013.01); *A61B 2017/00477* (2013.01);

(Continued)

(58) Field of Classification Search
CPC ............ A61B 17/7216; A61B 17/7225; A61B 17/663; A61B 17/7014; A61B 17/1725;
(Continued)

(56) References Cited

U.S. PATENT DOCUMENTS 6,336,929 B1 * 1/2002 Justin ................. A61B 17/7216
606/63
9,408,644 B2 * 8/2016 Zahrly ............... A61B 17/7216
(Continued)

OTHER PUBLICATIONS

Paley, D., "History of Implantable Limb Lengthening", www.mheresearchfoundation.org/files/Implantable_limb_lengthening.pdf (2014).
(Continued)

*Primary Examiner* — Pedro Philogene

(57) ABSTRACT

A bone adjustment device such as, for example, an intramedullary lengthening nail may include a first or outer body portion having a notch, a second or inner body portion, a threaded shaft coupled to the first body portion to rotate relative thereto, an inner magnet received by the first body portion and coupled to the threaded shaft for rotation therewith, and a threaded block positioned in the notch, the threaded block having internal threads, the threaded shaft passing through the threaded block and threadedly engaging with the internal threads. Various reconfiguration assembly embodiments include welding the threaded block to the first body portion, the notch being located a distance from the distal end of the first body portion, an overlapping arrangement between the first body portion and the second body portion, and a collar positioned over the first body portion.

16 Claims, 6 Drawing Sheets

(52) U.S. Cl.
CPC .............. *A61B 2017/00876* (2013.01); *A61B 2017/00991* (2013.01)

(58) Field of Classification Search
CPC ... A61B 17/921; A61B 17/68; A61B 17/8076; A61B 17/8004; A61B 17/7016; A61B 17/7291; A61B 50/30; A61B 50/33; A61B 50/34; A61B 2017/00991; A61B 2017/00876; A61B 2017/00411; A61B 2017/00398; A61B 2017/00477; A61B 2017/00845; A61B 2017/681
USPC ....................... 606/60, 62–65, 105, 246–279
See application file for complete search history.

(56) References Cited

U.S. PATENT DOCUMENTS

| | | | |
|---|---|---|---|
| 9,421,046 B2* | 8/2016 | Pool | A61B 17/84 |
| 2009/0254088 A1* | 10/2009 | Soubeiran | A61B 17/7216 606/63 |
| 2010/0049204 A1* | 2/2010 | Soubeiran | A61B 17/025 606/90 |
| 2011/0238126 A1* | 9/2011 | Soubeiran | A61B 17/7216 606/86 R |

OTHER PUBLICATIONS

Paley, D., et. al., "Limb Lengthening by Implantable Limb Lengthening Devices", Techniques in Orthopaedics, 29 (2):72-85 (2014).

\* cited by examiner

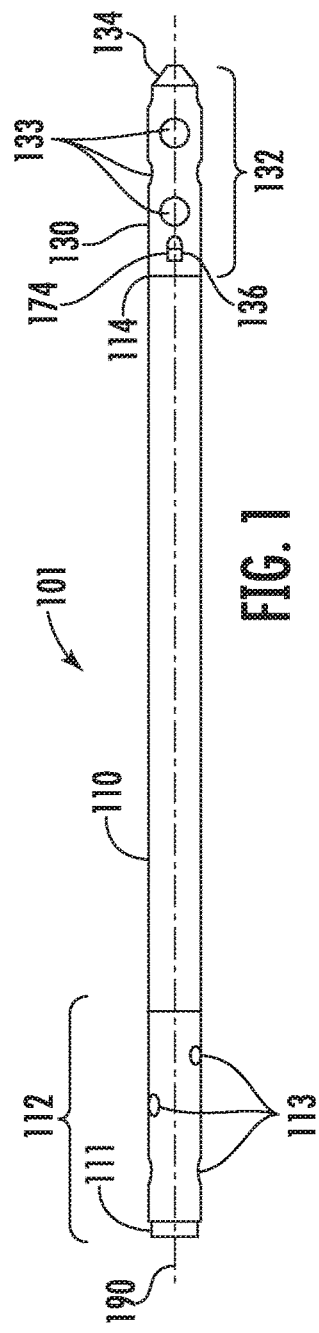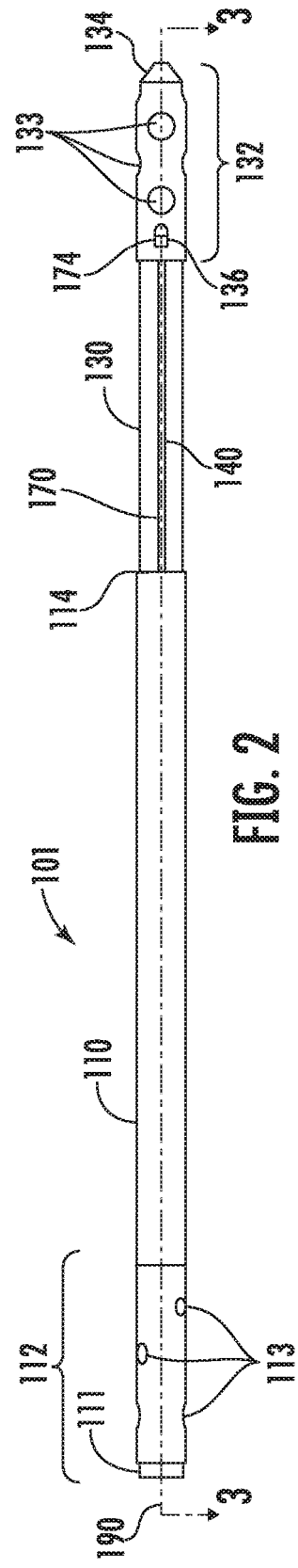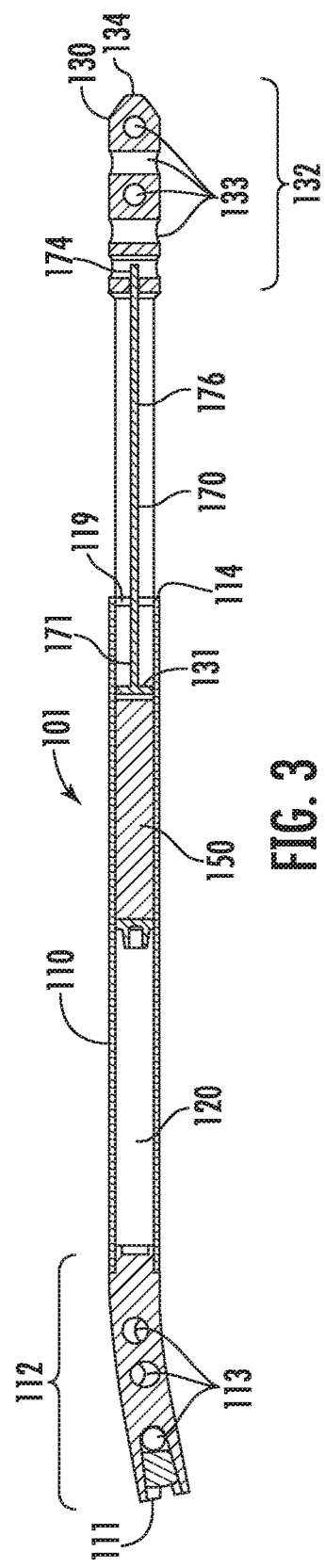

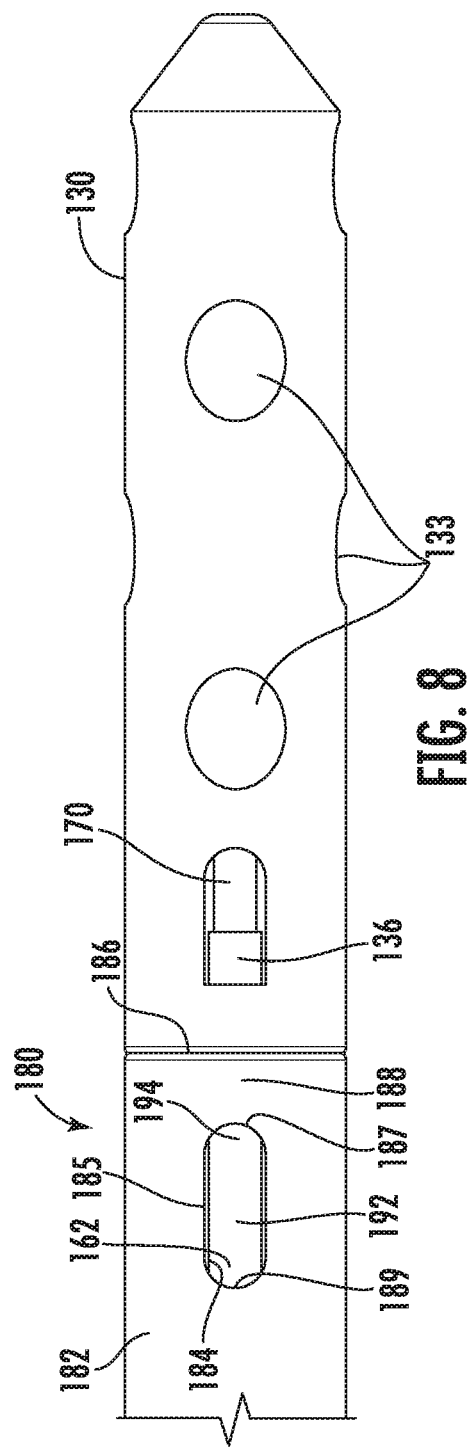

IMPLANTABLE BONE ADJUSTMENT DEVICES

CROSS-REFERENCE TO RELATED APPLICATIONS

This application claims priority to U.S. Provisional Patent Application Ser. No. 62/568,888, entitled "Implantable Bone Adjustment Devices," filed Oct. 6, 2017, the entirety of which application is incorporated by reference herein.

FIELD OF THE DISCLOSURE

The present disclosure generally relates to implantable reconfigurable bone adjustment devices, and more particularly, but not exclusively, relates to implantable reconfigurable bone adjustment devices that include one or more configurations to improve the strength of connections of various parts of the implantable reconfigurable bone adjustment devices.

BACKGROUND OF THE DISCLOSURE

Implantable reconfigurable bone adjustment devices are occasionally used in orthopedic procedures to gradually adjust the position, orientation, geometry and/or length of a bone, such as, for example, by distraction, compression, realignment or bone transport. One embodiment of an implantable reconfigurable bone adjustment device is a limb-lengthening nail (LLN) configured for implantation in the medullary canal of a long bone and subsequently manipulated to adjust the length of the bone. Another embodiment of an implantable reconfigurable bone adjustment device is a bone transport nail or rod configured for implantation in the medullary canal of a long bone and subsequently manipulated to move a middle bone fragment or segment across a gap between proximal and distal bone fragments to induce bone regeneration in the gap. Still other embodiments of implantable reconfigurable bone adjustment devices include spinal adjustment implants and implants configured to achieve other gradual adjustments to the shape, position or length of skeletal structures. As can be appreciated, the size of these devices that are implanted in the medullary canal may be limited by the size of the medullary canal which may also limit the strength of these devices.

Some embodiments of implantable reconfigurable bone adjustment devices include internal magnets that are configured to rotate upon actuation by an external actuating device, thereby driving a threaded rod that engages other device components to achieve a dimensional modification of the device or other relational modification between components of the device. Such dimensional modification or relational modification of the device operates on bone segments, portions or fragments to which the device is affixed to exert pressure on the bone segments, portions or fragments, thereby gradually moving the bone segments, portions or fragments relative to one another. Such devices include a first member or part configured to be affixed to a first bone segment, portion or fragment; a second member or part configured to be affixed to a second bone segment, portion or fragment; a rod with at least one thread, the rotation of which causes displacement of the second member or part relative to the first member or part, and a mechanism for controlling the rotation of the threaded rod.

In the case of certain LLN devices, for example, the second member or part is assembled telescopically relative to the first member or part and rotation of the threaded rod operates to telescopically displace the second member or part (which may be referred to as an inner body) relative to the first member or part (which may be referred to as an outer body), thereby increasing the distance between the bone segments, portions or fragments to which the first member or part and the second member or part are respectively affixed. In such LLN devices, the first member or part and/or the second member or part are configured to carry some amount of limb load and therefore may be prone to mechanical breakage for various reasons.

In use, rotation of the threaded rod may be driven by a component, referred to herein as a "drive mechanism," whose actuation is controlled to achieve a desired amount of rotation over time and at a desired rate, to achieve a desired amount of bone adjustment at a desired rate. In certain devices, the drive mechanism includes a magnet hermetically sealed in a housing, although other types of drive mechanisms, such as electric motors, are contemplated. A common feature of such drive mechanisms, which may also include gear reducers, is that the threaded rod is rigidly affixed to a structure of the drive mechanism to achieve controlled rotation of the threaded rod. This structure is referred to herein as a "driver." In such LLN devices, it is a delicate balance between the appropriate amount of mechanical advantage using the drive mechanism, the appropriate amount of strength from the torsion of the magnet, and the appropriate amount of strength from the LLN device itself along with the size requirements of the LLN devices. Often balancing all of these factors may lead to premature failure which results in the inability of the device to perform its intended bone adjustment action.

The threaded rod in such devices necessarily engages at least one component of the device (other than the driver) such that rotation of the threaded rod changes the relative positions of different device components. This at least one component (other than the driver) is typically an internally threaded block that is attached to the first member or part and configured to receive the threaded rod.

When LLN devices are implanted in a patient, there is a required amount of travel or movement of the outer body (e.g., first member or part) relative to the inner body (e.g., second member or part) that must be balanced against an acceptable amount of stress in the welded junction between the outer body and the threaded block. If the device is fully extended, then there is an increased possibility that the LLN device can fail under certain loading conditions.

One form of attachment of the internally threaded block to the first member or part includes welding. The rotation of the threaded rod imposes forces on the threaded rod, the internally threaded block, and the weld between the internally threaded block and the first member or part. Often the welded material is inherently weaker than the threaded block or the first member or part thereby causing a risk for failure at the weld junction if the implantable reconfigurable bone adjustment device is overloaded.

While currently available bone adjustment systems have produced excellent results, many of these devices exhibit one or more shortcomings or disadvantages that render the device susceptible to failure. For example, a problem that has been encountered is that the stress concentrations at the point where the threaded block is affixed to the first member or part can cause failure of the device at this junction. Failures of a device at this junction results in the inability of the device to perform its intended bone adjustment action.

For these reasons among others, a need remains for further improvements in this technological field. The present disclosure addresses this need.

SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure provides implantable reconfigurable bone adjustment devices, kits, systems and methods for moving first and second members of the device, and hence first and second bone segments, portions or fragments coupled thereto, with respect to one another.

In one embodiment, there is provided a reconfigurable bone adjustment device such as, for example, an intramedullary limb lengthening nail, that may include a first member, body portion, or outer body having a distal end opposite a proximal end, and a notch or opening positioned between the distal end and the proximal end. The device may also include a second member, body portion, or inner body having a portion received by the first member, a threaded shaft coupled to the first member to rotate relative thereto, an inner magnet received by the first member and coupled to the threaded shaft for rotation therewith, and a threaded block positioned in the notch and coupled to the first member, the threaded block having internal threads. The threaded shaft passing through the threaded block and threadedly engaging with the internal threads. The device may also include one or more reconfiguration assemblies that are configured to reduce applied stresses, such as axial forces, torsional forces, bending moments and/or eccentric moments on the first member/threaded block junction and/or by configuring the junction in a manner whereby one of more of the axial forces, torsional forces, bending moments and/or eccentric moments is isolated away from the junction or reduced. In one embodiment, the reconfiguration assembly includes welding at an angle between the threaded block and the first member. In another embodiment, the reconfiguration assembly includes an overlapping arrangement between the first member and an extended end portion of the second member. In another embodiment, the reconfiguration assembly includes positioning the notch a distance away from a distal end of the first member and positioning a collar over the notch and the threaded block positioned therein. Any of these reconfiguration assembly embodiments may be combined in an intramedullary lengthening nail embodiment.

In various embodiments, there is provided a reconfigurable bone adjustment device movable between a retracted state and an extended state. The bone adjustment device may include a first member configured for attachment to a first bone fragment; a second member configured for attachment to a second bone fragment, the second member including an elongated slot; a drive mechanism configured to move the second member relative to the first member; a threaded block fixedly coupled to the first member, the threaded block positioned within the elongated slot; a threaded rod having a proximal end operatively coupled to the drive mechanism, an intermediate portion threadably coupled to the threaded block, and a distal end operatively coupled to the second member so that rotation of the drive mechanism rotates the threaded rod and moves the second member relative to the first member; and means for reducing applied stresses at the junction between the threaded block and the first member.

In some embodiments, the first member includes a distal end, a proximal end, and a notch located between the distal end and the proximal end, at least a portion of the threaded block being positioned in the notch.

In some embodiments, the threaded block includes a proximal end and a distal end, the proximal end including an arcuate shape and the notch includes a proximal end and a distal end, the proximal end of the notch including a corresponding arcuate shape configured to receive the proximal end of the threaded block.

In some embodiments, the proximal end of the threaded block includes a radius and the proximal end of the notch includes a corresponding radius to receive the proximal end of the threaded block.

In some embodiments, the distal end of the threaded block is substantially flush with the distal end of the first member.

In some embodiments, the threaded block is coupled to the first member by a weld positioned along a junction between the threaded block and the notch formed in the first member.

In some embodiments, the weld is applied by a laser beam that is positioned at an angle relative to the threaded block and the first member, the angle being between about 10 degrees to about 35 degrees.

In some embodiments, the weld includes depositing a first weld at a first angle to a first portion of the junction and depositing a second weld at a second angle to a second portion of the junction.

In some embodiments, the first weld is applied at a first energy and the second weld is applied at a second energy, the second energy is different from the first energy.

In some embodiments, the first portion is the arcuate proximal end of the notch and the second portion includes a leg portion of the notch.

In some embodiments, the threaded block is welded to the first member by one of varying a weld angle and an energy level of a laser beam during welding.

In some embodiments, a first weld is applied along the arcuate shape proximal end of the threaded block and the notch includes a first energy and a first angle, a second weld is applied along straight portions of the threaded block and the notch include a second energy and a second angle.

In some embodiments, the second energy level and the second angle are greater than the first energy level and the first angle.

In some embodiments, the first member includes a notch positioned adjacent to a distal end thereof, at least a portion of the threaded block being positioned in the notch.

In some embodiments, the notch has an elongated shape that includes a center portion that spans between a distal notch end portion and a proximal notch end portion, the proximal notch end portion including a semi-circular shape for contacting a corresponding semi-circular shape formed on a proximal end portion of the threaded block.

In some embodiments, the distal notch end portion includes a semi-circular shape for contacting a corresponding semi-circular shape formed on a distal end portion of the threaded block.

In some embodiments, the first member is an outer body having a distal end and a proximal end, the outer body including a notch positioned between the distal end and the proximal end, at least a portion of the threaded block is positioned in the notch and the second member is an inner body having a distal end and a proximal end, a portion of the proximal end of the inner body is received within the outer body so that an overlap portion is formed between the distal end of the outer body and the proximal end of the inner body when the bone adjustment device is in the extended state.

In some embodiments, the portion of the proximal end of the inner body extends from an end of the elongated slot formed in the inner body to the proximal end of the inner body.

In some embodiments, the first member includes a notch extending through a surface thereof, the notch positioned adjacent to a distal end of the first member, the notch including a distal end portion, a proximal end portion, and a center portion, the proximal and distal end portions of the notch each including a semi-circular shape.

In some embodiments, the threaded block includes a proximal end and a distal end, the proximal and distal ends of the threaded block each including a semi-circular shape for contacting the semi-circular shape proximal and distal ends of the notch.

In some embodiments, the first member includes a notch formed therein, the notch being positioned near a distal end of the first member, the notch being sized and configured to receive a portion of the threaded block therein, the bone adjustment device further comprising a collar sized and configured to be positioned over the notch and the threaded block positioned within the notch for coupling the threaded block to the first member.

In some embodiments, the first member includes a main body portion having a first outer diameter and a distal end portion having a second outer diameter, the first outer diameter portion being larger than the second outer diameter, the distal end portion including a notch for receiving the threaded block therein.

In some embodiments, a collar is provided for slidably receiving the distal end portion of the first member to secure the threaded block to the first member.

In some embodiments, the collar is attached to the distal end portion by a press-fit configuration.

In some embodiments, the collar is attached to the distal end portion by a weld.

Further features and advantages of at least some of the embodiments of the present disclosure, as well as the structure and operation of various embodiments of the present disclosure, are described in detail below with reference to the accompanying drawings.

BRIEF DESCRIPTION OF THE DRAWINGS

By way of example, a specific embodiment of the disclosed device will now be described, with reference to the accompanying drawings, in which:

FIG. 1 illustrates a side view of an example embodiment of an intramedullary limb lengthening nail, the limb lengthening nail illustrated in a retracted or contracted state;

FIG. 2 illustrates a side view of the intramedullary limb lengthening nail shown in FIG. 1, the limb lengthening nail illustrated in an extended or distracted state;

FIG. 3 illustrates a cross-sectional view of the limb lengthening nail shown in FIG. 2, taken along line 3-3;

FIG. 8 illustrates a partial plan view of an alternate, example embodiment of an intramedullary limb lengthening nail in accordance with one embodiment of the present disclosure;

Figure 4:
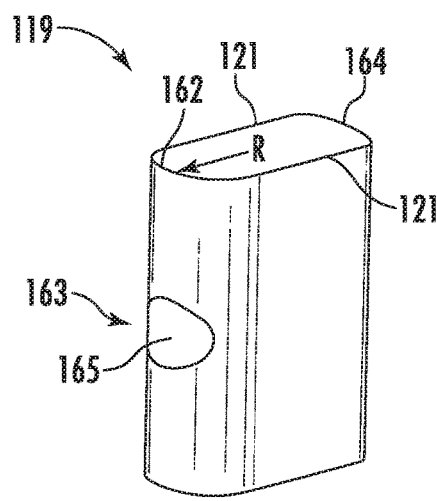
FIG. 4 illustrates a perspective view of an example embodiment of a threaded block that can be used in connection with the intramedullary limb lengthening nail shown in FIGS. 1-3 in accordance with one embodiment of the present disclosure.

It should be understood that the drawings are not necessarily to scale and that the disclosed embodiments are sometimes illustrated diagrammatically and in partial views. In certain instances, details which are not necessary for an understanding of the disclosed methods and devices or which render other details difficult to perceive may have been omitted. It should be further understood that this disclosure is not limited to the particular embodiments illustrated herein.

DETAILED DESCRIPTION

For the purposes of promoting an understanding of the principles of the present disclosure, reference will now be made to the embodiments illustrated in the figures and specific language will be used to describe the same. It will nevertheless be understood that no limitation of the scope of the present disclosure is thereby intended. Any alterations and further modifications in the described embodiments, and any further applications of the principles of the present disclosure as described herein are contemplated as would normally occur to one skilled in the art to which the present disclosure relates.

Various embodiments of implantable reconfigurable bone adjustment devices are disclosed herein. In some embodiments, the implantable reconfigurable bone adjustment devices may include a first member, part, body portion, or component (used interchangeably herein without the intent to limit), a second member, and a rotatable threaded rod that engages at least one component affixed to first member and at least one component operable to axially move the second member relative to the first member. The implantable reconfigurable bone adjustment device also includes a drive mechanism to controllably actuate rotation of the threaded rod. In certain embodiments, the drive mechanism may be an internal magnet coupled to the threaded rod such that rotation of the internal magnet drives rotation of the threaded rod. This can be achieved, for example, by fixing the threaded rod directly to the internal magnet or a casing in which the internal magnet is contained, or can be achieved by connecting the threaded rod indirectly to the internal magnet, such as through a gear mechanism or other structure positioned therebetween. As described further herein, torque is applied to the internal magnet by applying a rotating magnetic field across the internal magnet from an external source. In other implantable reconfigurable bone adjustment device embodiments, rotation of the threaded rod may be controlled or driven by a drive mechanism other than an internal magnet. Alternative drive mechanisms for driving the threaded rod may include any other known or hereafter developed drive mechanisms known to a person of ordinary skill in the art including, for example, an electric motor with or without gear reducer, a current source inside or outside the patient's body, a permanent magnet with a gear reducer and a rotating magnetic field source external to the patient, etc. In alternate embodiments, the drive mechanism can be configured to drive the threaded rod in one direction only, or in both directions, according to requirements.

One representative, but non-limiting, example embodiment, of an implantable reconfigurable bone adjustment device contemplated by the present disclosure is an intramedullary limb lengthening nail, such as intramedullary ("IM") limb lengthening nail 101 depicted in FIGS. 1-3. Further details regarding representative IM limb lengthening nails are available in U.S. Pat. No. 8,777,947, which is hereby incorporated herein by reference in its entirety. Referring to FIGS. 1-3, the IM lengthening nail 101 may include a proximal body portion 110, a distal body portion 130, and a threaded rod 170 operatively associated with the proximal body portion 110 and the distal body portion 130. In use, rotation of the threaded rod 170 causes the proximal body portion 110 and the distal body portion 130 to move with respect to one another. In one embodiment, as will be described in greater detail, the proximal body portion 110 may be configured as an outer body and the distal body portion 130 may be configured as an inner body so that at least a portion of the distal body portion 130 may be received within at least a portion of the proximal body portion 110. Alternatively, it is envisioned that the proximal body portion may be configured as the inner body and the distal body portion may be configured as the outer body. In one embodiment, the threaded rod 170 may be mounted in and coupled to the distal body portion 130.

Each of the proximal body portion 110, the distal body portion 130, and the threaded rod 170 has a proximal end 111, 131, 171 and a distal end 114, 134, 174, respectively. The IM limb lengthening nail 101 may also include an inner magnet 150 (also referred to herein as "internal magnet") seated in the proximal body portion 110 and coupled to the proximal end 171 of the threaded rod 170, a distal block 136 coupled to the distal body portion 130 and a distal end 174 of the threaded rod 170, and a threaded block 119 coupled to the proximal body portion 110 and engaged with the threaded rod 170. The term "inner" or "internal" is used herein in reference to the magnet 150 to distinguish this magnet from a different magnet or multiple different magnets employed by an external actuator as described in greater detail below, which magnet or magnets of an external actuator, are referred to as "outer magnets." While neodymium magnets are suggested, other magnets may be employed as will be apparent to those skilled in the art.

The proximal body portion 110 may be at least partially hollow, having an inner wall 120 that defines an internal cylindrical chamber, for accommodating, inter alia, a portion of the distal body portion 130, which extends through the distal end 114 of the proximal body portion 110. The proximal and distal body portions 110, 130 are dimensioned such that the proximal and distal body portions 110, 130 can move in both axial directions with respect to one another. The proximal body portion 110 may also house the inner magnet 150, which may be mounted in a casing or carrier to facilitate the coupling of the inner magnet 150 to the threaded rod 170. The inner magnet 150 may include at least one permanent magnet, one of the poles of which is directed in one radial direction relative to a longitudinal axis 190 of the IM limb lengthening nail 101 and the other pole directed in an opposite radial direction relative to longitudinal axis 190. As described in further detail below, the inner magnet 150 may be rotated about the longitudinal axis 190 of the IM limb lengthening nail 101 by application of an externally applied rotating magnetic field. The IM limb lengthening nail 101 may also include a first locking portion 112 and a second locking portion 132, each of which includes a plurality of fastener openings 113, 133 structured to receive fasteners for coupling the respective ends of the IM limb lengthening nail 101 to the patient's bone.

The inner magnet 150 is coupled to the threaded rod 170, which extends through the proximal end 131 of the distal body portion 130. The threaded rod 170 may also extend through a bearing (not shown) which engages the inner wall 120 of the proximal body portion 110. Similarly, a bearing may be coupled to a proximal end of the inner magnet 150 to facilitate rotation of the inner magnet 150 within the proximal body portion 110. The distal end 174 of the threaded rod 170 is engaged with the distal block 136, which is coupled to the distal body portion 130. In use, the distal block 136 permits rotation of the threaded rod 170 with respect to the distal body portion 130 and couples the distal body portion 130 and the threaded rod 170 for joint movement along the longitudinal axis 190. For example, the distal block 136 may be coupled or affixed to the distal body portion 130 such that the threaded rod 170 can rotate freely without altering the position of the distal end 174 of the threaded rod 170 with respect to the distal body portion 130. The threaded rod 170 also extends through the threaded block 119, which is coupled to the proximal body portion 110.

The threaded rod 170 may include a set of external threads 176 which are engaged with a set of internal threads formed in a threaded bore 165 (FIG. 4) of the threaded block 119. As noted above, the threaded rod 170 is axially coupled to the distal body portion 130 and is axially and rotationally coupled to the inner magnet 150, and the threaded block 119 is engaged with the threaded rod 170 and axially and rotationally coupled to the proximal body portion 110. As a result, rotation of the inner magnet 150 causes relative movement of the proximal and distal body portions 110, 130 along the longitudinal axis 190.

Figure 5A:
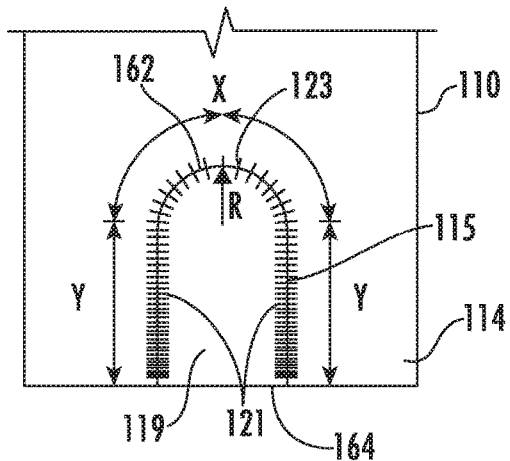
FIG. 5A illustrates a partial plan view of the threaded block shown in FIG. 4, the threaded block shown welded to the intramedullary limb lengthening nail shown in FIGS. 1-3.

With additional reference to FIGS. 4 and 5A, the threaded block 119 includes a proximal end 162 and a distal end 164. In the illustrated example embodiment, the proximal end 162 has an arcuate or semi/half-cylindrical shape that is configured to engage a notch or opening 115 formed in the proximal body portion 110 (notch and opening used interchangeably herein without the intent to limit). As such, in one embodiment, the proximal end 162 has a radius, R, and the notch 115 is sized with a corresponding radius to receive the proximal end 162 of the threaded block 119 therein. In other embodiments, the proximal end 162 and the notch 115 can have different shapes. The threaded block 119 also includes an opening 163 formed in the proximal end 162, and a threaded bore 165 extending through at least a portion of the length of the threaded block 119. The threaded bore 165 includes a set of internal threads (not illustrated) formed therein. The threaded block 119 may be coupled or mounted to the proximal body portion 110 in various configurations. In one embodiment, the proximal body portion 110 includes the notch 115 that extends through the inner wall 120 formed in the distal end 114 of the proximal body portion 110, and the threaded block 119 may be mounted in the notch 115. The notch 115 has a shape configured to receive and contact portions of the threaded block 119.

FIG. 1 illustrates the IM limb lengthening nail 101 in a retracted or contracted state, and FIGS. 2 and 3 illustrate the IM limb lengthening nail 101 in an extended or distracted state. The IM limb lengthening nail 101 may be moved between the contracted and distracted states by rotating the inner magnet 150 by application of an externally applied rotating magnetic field. More specifically, rotation of the inner magnet 150 may cause rotation of the threaded rod 170 and hence movement of the distal body portion 130 relative to the proximal body portion 110 along the longitudinal axis 190, thereby adjusting the length of the IM limb lengthening nail 101. As is evident from a comparison of FIGS. 1 and 2, the longitudinal positions of the distal block 136 and the distal end 174 of the threaded rod 170 with respect to the distal body portion 130 remain unchanged. That is, the distal body portion 130 may include an elongated slot 140 which enables the threaded block 119 to slide along the distal body portion 130 during relative movement of the proximal and distal body portions 110, 130 along the longitudinal axis 190.

In use, the IM limb lengthening nail 101 is configured for implantation in a bone having a medullary canal. Typically, the IM limb lengthening nail 101 is implanted such that the first locking portion 112 is affixed to a first bone portion and the second locking portion 132 is affixed to a second bone portion, and a gap separates the first and second bone portions. The gap may be formed, for example, during an osteotomy procedure in which the bone is severed for purposes of lengthening the bone over time. The IM limb lengthening nail 101 is implanted into the medullary canal of the bone and is surgically coupled to the bone. For example, the proximal body portion 110 is coupled to the first bone portion and the distal body portion 130 is coupled to the second bone portion by fasteners such as screws or pins, which may be received in or otherwise engaged with the openings 113, 133.

Both distraction and compaction of the proximal and distal body portions 110, 130 with respect to each other is possible. Thus, with the IM limb lengthening nail 101 implanted in the bone, the segmented portions of the bone may be distracted or compacted as necessary by rotation of the threaded rod 170 and the inner magnet 150 in a first direction or a second direction, respectively, thereby enabling lengthening or shortening of the bone. In other words, the telescoping ability allows the IM limb lengthening nail 101 to both distract and contract the bone portions, to which the proximal and distal body portions 110, 130 are coupled. During lengthening, the IM limb lengthening nail 101 may be transitioned from the retracted state (FIG. 1) to the expanded state (FIG. 2), thereby lengthening the bone. The IM limb lengthening nail 101 may be transitioned from the retracted state to the expanded state gradually over a given period of time, such that an ossified region forms as the bone lengthens and heals.

It should be understood that the principles and features of the present disclosure are not limited to use with the IM limb lengthening nail illustrated and described in connection with FIGS. 1-3 and that the principles and features may be used in combination with other IM limb lengthening nails.

Figure 5B:
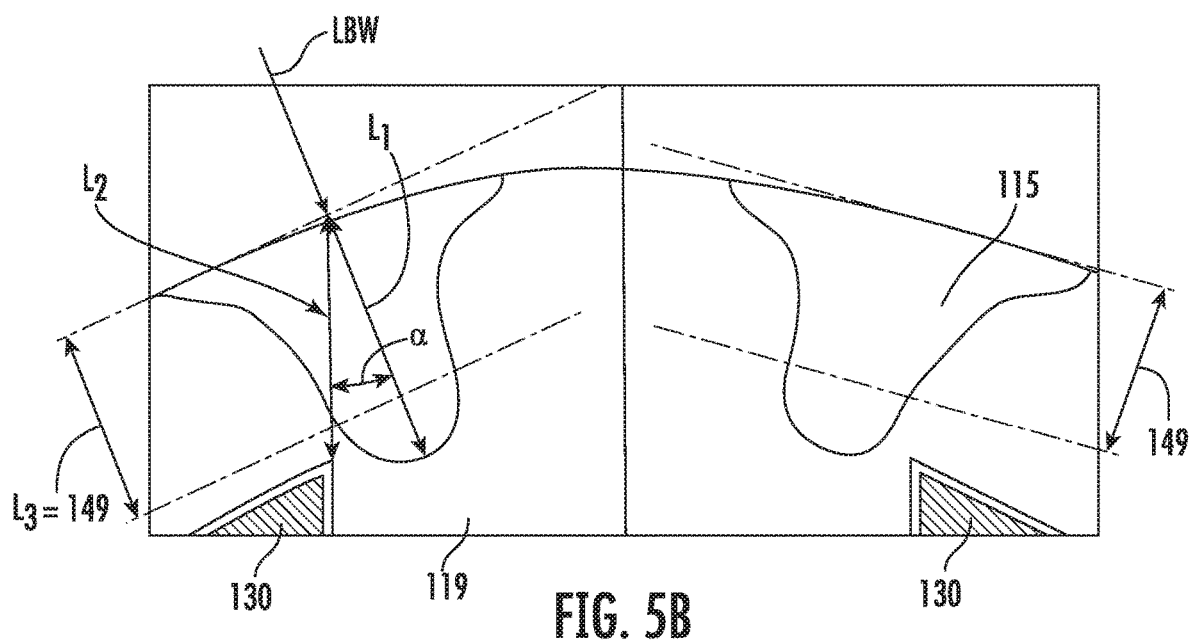
FIG. 5B illustrates an example embodiment of a weld used to couple the threaded block to the intramedullary limb lengthening nail as shown in FIG. 5A.

In one embodiment illustrated in FIGS. 5A and 5B, one technique used to attach the threaded block 119 to the proximal body portion 110 includes positioning the threaded block 119 in the notch 115 such that the proximal end 162 of the threaded block 119 is positioned against an arcuate portion 123 of the notch 115 and the distal end 164 of the threaded block 119 is substantially flush with the distal end 114 of the proximal body portion 110. The threaded block 119 and the proximal body portion 110 may then be welded together via, for example, a laser beam. In other embodiments, the threaded block 119 can be attached to the proximal body portion 110 in other configurations and by other techniques and/or including this technique. In the example embodiment illustrated in FIGS. 5A and 5B, the strength of the connection between the threaded block 119 and the proximal body portion 110 is increased by increasing the effective penetration depth of the welds that are used to attach and couple or mount the threaded block 119 to the proximal body portion 110. In one embodiment, the fatigue strength of the weld is increased by 5 times over other techniques of welding that do not include applying the weld at an angle.

For various reasons, the interior wall 120 of the proximal body portion 110 is often thin, and as such there is a risk of penetrating the interior wall 120 of the proximal body portion 110 with the weld and/or depositing weld spatter on the internal components of the IM limb lengthening nail 101. For example, deposition of weld spatter on the interior wall 120 of the proximal body portion 110 and the distal body portion 130 can be problematic as the threaded rod 170 and the inner magnet 150 move relative to the proximal body portion 110. It is beneficial if the interior wall 120 of the proximal body portion 110 remains free of debris to avoid limiting movement of the distal body portion 130 and the threaded rod 170 and thereby decreasing the effectiveness of the IM limb lengthening nail 101. It was found that aiming the laser beam directly, i.e., as measured relative to a line substantially perpendicular to the proximal body portion 110 at the application site of the laser beam, onto the junction of the threaded block 119 and the proximal body portion 110 to increase the effective penetration depth of the weld was problematic in that there is an increased risk that the weld may penetrate to the interior wall 120 of the proximal body portion 110 and/or deposit debris.

Therefore, it was unexpectedly found that varying one or more of the angle and energy level of the laser beam during welding increased the strength of the welded connection between the threaded block 119 and the proximal body portion 110 that are joined. Moreover, it was unexpectedly found that increasing the angle of the laser beam for the corresponding weld, also increased an effective penetration depth of the weld 149 and avoided any flow of the weld onto the interior wall 120 of the proximal body portion 110 and the distal body portion 130. Moreover, the weld spatter deposit onto the interior wall 120 of the proximal body portion 110 was avoided and the weld may flow into the threaded block 119; however, this encroachment does not affect operability of the IM limb lengthening nail 101. In particular, referring to FIG. 5B, it was found that by aiming the laser beam along a line LBW that is positioned at an offset angle α relative to a line that is substantially perpendicular to the proximal body portion 110 at the application site of the laser beam, increased the effective penetration depth of the weld 149. In one example embodiment, the offset angle α may be approximately 25 degrees.

Weld penetration may be affected by any number of variables, for example, workpiece mass, laser weld focus depth, or shielding gas configuration. Larger or smaller workpieces may require more or less deposited energy for effective results. Generally, the relationship may be expressed as L1>L2≥L3 where the energy required to produce the equivalent weld penetrations are E1>E2≥E3, respectively. As illustrated in FIG. 5B, L1 is the weld penetration, L2 is the joint depth, and L3 is the effective penetration depth of the weld 149, wherein E1, E2, and E3 are the required energies to produce welds of equivalent L1, L2, and L3 depths.

In one embodiment, a first weld X having a first energy and a first angle is applied to the arcuate portion 123 of the notch 115 and the proximal end 162 of the threaded block 119 to weld or attach the threaded block 119 to the proximal body portion 110. A second weld Y having a second energy and a second angle is applied to a leg portion 121 (FIG. 4) of the threaded block 119 and the proximal body portion 110 to further attach the threaded block 119 to the proximal body portion 110. Both the first angle and the second angle are measured relative to a line perpendicular to the proximal body portion 110 at the point of application of the laser beam. In one embodiment, the second energy level and the second angle are greater than the first energy level and the first angle. In another embodiment, one of the first weld having the first energy or the second weld having the second energy is applied to both the arcuate portion 123 and the leg portion 121 of the threaded block 119 and the proximal body portion 110, respectively, such that a single weld is applied to the arcuate portion 123 and the leg portions 121. The first angle and the second angle can be between about 10 degrees to about 35 degrees. In one embodiment, the first angle and the second angle are about 25 degrees. The first energy level and the second energy level are about 10 to about 30 Joules. In one embodiment, the energy level is about 20 Joules.

Figure 6:
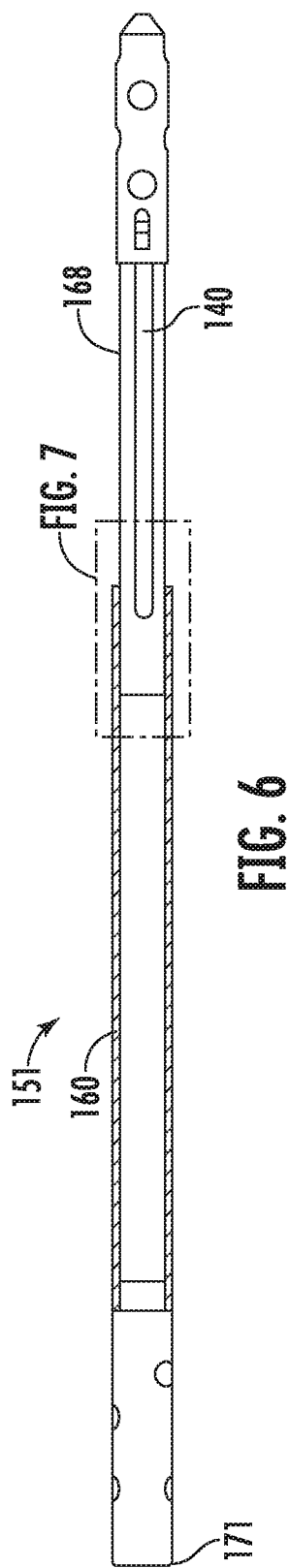
FIG. 6 illustrates a cross-sectional view of an alternate, example embodiment of an intramedullary limb lengthening nail in accordance with one embodiment of the present disclosure.
Figure 7:
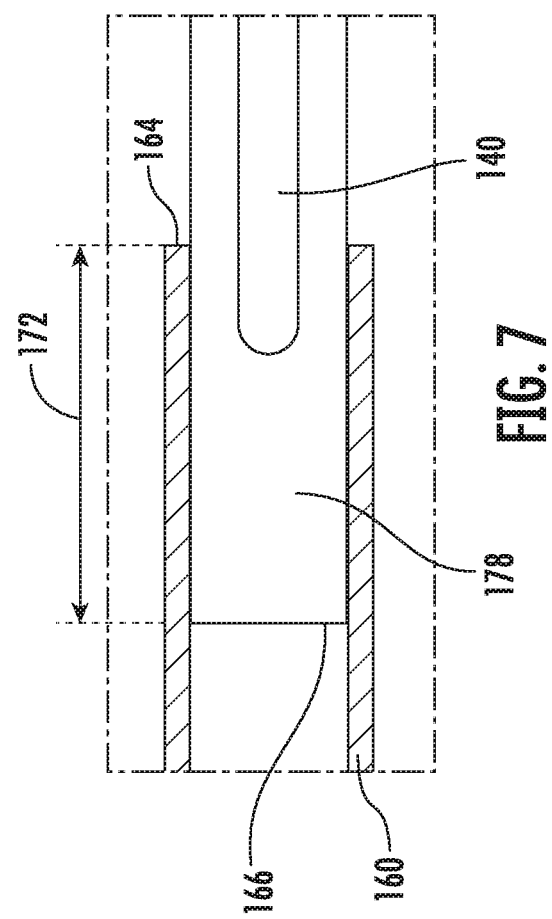
FIG. 7 illustrates a detailed view of the intramedullary limb lengthening nail shown in FIG. 6.

Referring to FIGS. 6 and 7, an alternate example embodiment of an implantable reconfigurable bone adjustment device is illustrated. As illustrated, the implantable reconfigurable bone adjustment device may be an IM limb lengthening nail 151. The IM limb lengthening nail 151 is similar to the IM limb lengthening nail 101 described above, therefore similar parts will not be described for the IM limb lengthening nail 151 for the sake of brevity. Generally, when the IM limb lengthening nail is implanted in a patient, there is a preferred amount of available travel or movement of the distal body portion 168 relative to the proximal body portion 160 that should be balanced against an acceptable amount of stress in the welded junction between the proximal body portion 160 and the threaded block 119. In a fully extended position, there is an increased possibility of failure of any IM limb lengthening nail under certain loading conditions. However, when the IM limb lengthening nail is implanted in a patient, it is preferred that a maximum amount of movement or stroke of the distal body portion 161 relative to the proximal body portion 160 be available without failure of the device. As illustrated, in one example embodiment, the IM limb lengthening nail 151 includes a proximal body portion (e.g., an outer body 160) similar to the proximal body portion (e.g., outer body 110); however, the outer body 160 of IM limb lengthening nail 151 includes an overlap portion 172 that is measured from a distal end 164 towards a proximal end 171 of the outer body 160. The IM limb lengthening nail 151 includes a distal body portion 168 (e.g., an inner body) similar to distal body portion 130 (e.g., inner body); however, the inner body 168 includes an end portion 178 that extends a longer distance than an end portion of the distal body portion 130 (e.g., inner body). In particular, the overlap portion 172 covers a proximal end 166 of the inner body 168 and also covers the end portion 178 of the inner body 168 in a fully extended state. The end portion 178 extends from an end of the elongated slot 140 to the proximal end 166 of the inner body 168. In one embodiment, the end portion 178 was increased by an amount between 40-70% longer than an end portion of the distal body portion 130 (e.g., inner body). It has been discovered that the combination of the overlap portion 172 covering the end portion 178 and the end portion 178 being longer, reduces the stress in the welded junction between the outer body 160 and the threaded block 119. In one embodiment, the stress is reduced by about 40% when the length of the end portion 178 and coverage of the end portion 178 with the overlap portion 172 was increased by about 65%. It was also discovered that in a fatigue test where the IM limb lengthening nail 151 was tested to clinical limits, the IM limb lengthening nail 151 met the minimum standards or expectations. In one embodiment, the overlap portion 172 may be between 12 mm and 40 mm, preferably about 25 mm.

Referring to FIG. 8, an alternate example embodiment of an implantable reconfigurable bone adjustment device is illustrated. As illustrated, the implantable reconfigurable bone adjustment device may be an IM limb lengthening nail 180. The IM limb lengthening nail 180 is similar to IM limb lengthening nail 101 described above, therefore similar parts will not be described for the IM lengthening nail 180 for the sake of brevity. The IM limb lengthening nail 180 includes a proximal body portion (e.g., an outer body) 182 similar to the proximal body portion (e.g., outer body) 110; however, the outer body 182 in the IM limb lengthening nail 180 includes a notch 184 that extends through the outer and inner walls near a distal end 186 of the outer body 182. As illustrated, the notch 184 may include an elongated shape that includes a center portion 185 having a pair of edges that span between a distal end portion 187 and a proximal end portion 189 wherein the distal end portion 187 and the proximal end portion 189 each have a semi-circular shape and a corresponding radius. The notch 184 may be configured and sized to receive a threaded block 192 therein. As illustrated, the outer body 182 includes a distal end portion 188 that is positioned between the notch 184 and the distal end 186. Beneficially, the combination of the distal end portion 188 and the location of the notch 184 being positioned a distance from the distal end 186 removes or limits a crack initiation site of the outer body 182 near the distal end 186. The threaded block 192 is similar to the threaded block 119; however, the threaded block 192 includes a distal end 194 opposite a proximal end 162 wherein the distal end 194 and the proximal end 162 each have an arcuate or half-cylindrical shape that is configured to engage the distal end portion 187 and the proximal end portion 189, respectively, of the notch 184 formed in the outer body 182. Both the distal end 194 and the proximal end 162 each have a radius that corresponds to a similar radius for the distal end portion 187 and the proximal end portion 189, respectively, of the notch 184 such that the notch 184 is sized to receive and retain the threaded block 192 therein. In other embodiments, the proximal end 162, the distal end 194, the proximal end portion 189, and the distal end portion 187 can have correspondingly different shapes. In the illustrated embodiment, the threaded block 192 is coupled or mounted in the notch 184 in a press fit configuration or other fitting arrangement. Alternatively, or additionally, the threaded block 192 can be welded to the notch 184 wherein the weld fully encircles the threaded block 192 and the notch 184. In other embodiments, the threaded block 192 is coupled or mounted to the notch 184 in another manner. The threaded block 192 also includes an opening (not illustrated) similar to opening 163 formed in the threaded block 119.

Figures 9A, 9B, 9C:
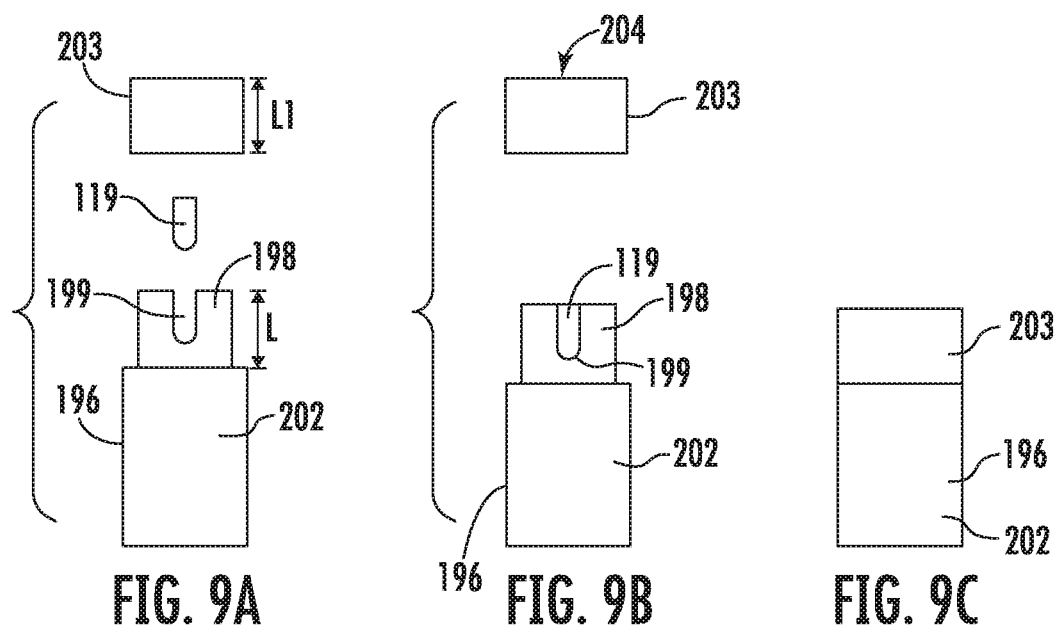
FIG. 9A illustrates an exploded, partial plan view of an alternate, example embodiment of an intramedullary limb lengthening nail in accordance with one embodiment of the present disclosure.
FIG. 9B illustrates an exploded, partial plan view of the intramedullary limb lengthening nail shown in FIG. 9A.
FIG. 9C illustrates a partial plan view of the intramedullary limb lengthening nail shown in FIG. 9B.

Referring to FIGS. 9A, 9B, and 9C, an alternate example embodiment of an implantable reconfigurable bone adjustment device is illustrated. As illustrated, a proximal body portion (e.g., an outer body) 196 of the IM limb lengthening nail is similar to proximal body portion (e.g., outer body) 110 of the IM limb lengthening nail 101 described above, therefore similar parts will not be described for the IM lengthening nail for the sake of brevity. As illustrated, in the example embodiment, the outer body 196 includes a distal end portion 198 that has a length L sized to receive a notch 199 and an adjacent portion (or main body portion) 202 that spans from the distal end portion 198 towards a proximal end (not illustrated). The distal end portion 198 has a tubular shape with an outside diameter that is smaller than an outside diameter of the adjacent portion 202. The distal end portion 198 is sized to receive a collar 203 thereon. The notch 199 is similar to the notch 115 therefore it will not be described again. The collar 203 has a tubular shape with a length, LI, and an opening 204 that are sized to fit over the distal end portion 198 when assembled. The collar 203 has an outside diameter that corresponds to the outside diameter of the adjacent portion 202 to form a substantially smooth surface when the collar 203 is assembled with the outer body 196. The notch 199 is sized to receive the threaded block 119, therefore the collar 203 will cover the threaded block 119 and the notch 199 when assembled. The threaded block 119 can be assembled with the notch 199 by welding, a press fit arrangement, or other techniques. The collar 203 can form a press fit connection with the distal end portion 198 of the outer body 196 or the collar 203 can be welded to the distal end portion 198. In other embodiments, the collar 203 can be assembled with the distal end portion 198 by other techniques.

In one embodiment, the length of the notch 199 is between about 6 to about 11 millimeters. Further, the length L of the distal end portion 198 is between about 8 and 9 millimeters. The outer diameter of the collar 203 is between about 8 to about 11 millimeters, with a wall thickness of about 0.5 millimeters. In one embodiment, the wall thickness of the adjacent portion 202 is about 1.0 millimeters, the wall thickness of the distal end portion 198 is about 0.5 millimeters, and the wall thickness of the collar 203 is about 0.5 millimeters. In other embodiments, the dimensions of the distal end portion 198, the collar 203, and the adjacent portion 202 can be different.

As can be appreciated, many of the embodiments or portions of embodiments described herein can be combined into a single embodiment of the IM limb lengthening nail.

While the IM limb lengthening nail is described as a representative implantable reconfigurable bone adjustment device, it is to be understood that the present disclosure in not limited to use with an IM limb lengthening nail, it being understood that the present disclosure finds advantageous use with a variety of other implantable reconfigurable bone adjustment devices that include a drive mechanism operable to controllably rotate a driver component that is coupled to a threaded rod to drive rotation of the threaded rod to move first and second members of the device relative to one another.

As indicated above, to rotate the rotatable portion of an implantable reconfigurable bone adjustment device that employs a drive mechanism comprising an internal magnet, such as, for example, a rotatable internal magnet 150 that is coupled to a threaded rod 170 of the device, a rotating magnetic field may be applied to the implantable reconfigurable bone adjustment device to apply torque to the internal magnet. In one embodiment, this torque is applied by magnetically coupling an external magnetic actuator with the rotatable internal magnet 150.

The creation of a magnetic driving field for rotating the internal magnet 150 and the threaded rod 170 coupled coaxially therewith can be accomplished by any suitable mechanism now known or hereafter developed. In one embodiment, an external actuator, also referred to herein as an actuation unit, may be used to actuate rotation of the internal magnet 150 following implantation of the IM limb lengthening nail 101 in a skeletal position of a patient. In one embodiment, the external actuator is operable to position a driving magnet, also referred to herein as an outer magnet, near the implanted reconfigurable bone adjustment device, but external to the patient, at the height of the internal magnet 150. The external actuating mechanism is designed and positioned to maximize torque to the internal magnet 150 and the threaded rod 170, in any event, to provide sufficient torque to rotate the internal magnet 150 despite the distance between the internal magnet 150 and the one or more outer magnets in the actuation unit and applied resisting forces on the implantable reconfigurable bone adjustment device (e.g., IM limb lengthening device). In this regard, rotation of the internal magnet 150 must overcome any compressive load imparted between the components of implantable reconfigurable bone adjustment device by bone tissue and other tissues of the patient, together with internal frictional forces of the implantable reconfigurable bone adjustment device.

In the presence of a magnetic driving field perpendicular to the rotational axis of the internal magnet 150 (which lies on the longitudinal axis 190) and rotating around the rotational axis, the internal magnet 150 tends to become oriented in the magnetic driving field, which applies a torque to the internal magnet 150 and causes the internal magnet 150 to rotate in the same rotational direction of the magnetic driving field, together with the threaded rod 170 that is coupled coaxially with the internal magnet 150, if the applied torque is greater than the load torque on the threaded rod 170 under the load applied to it at the time when the magnetic driving field is activated.

In one embodiment, the driving magnet includes at least one permanent magnet, one of the poles of which is directed towards the longitudinal axis 190. In another embodiment, an even greater torque can be applied to the internal magnet 150 by using two permanent driving magnets positioned such that the south pole of one is facing the north pole of the other, and such that the implantable reconfigurable bone adjustment device and the part of the patient's body that surrounds the implantable reconfigurable bone adjustment device are positioned between the two permanent magnets.

Figure 10:
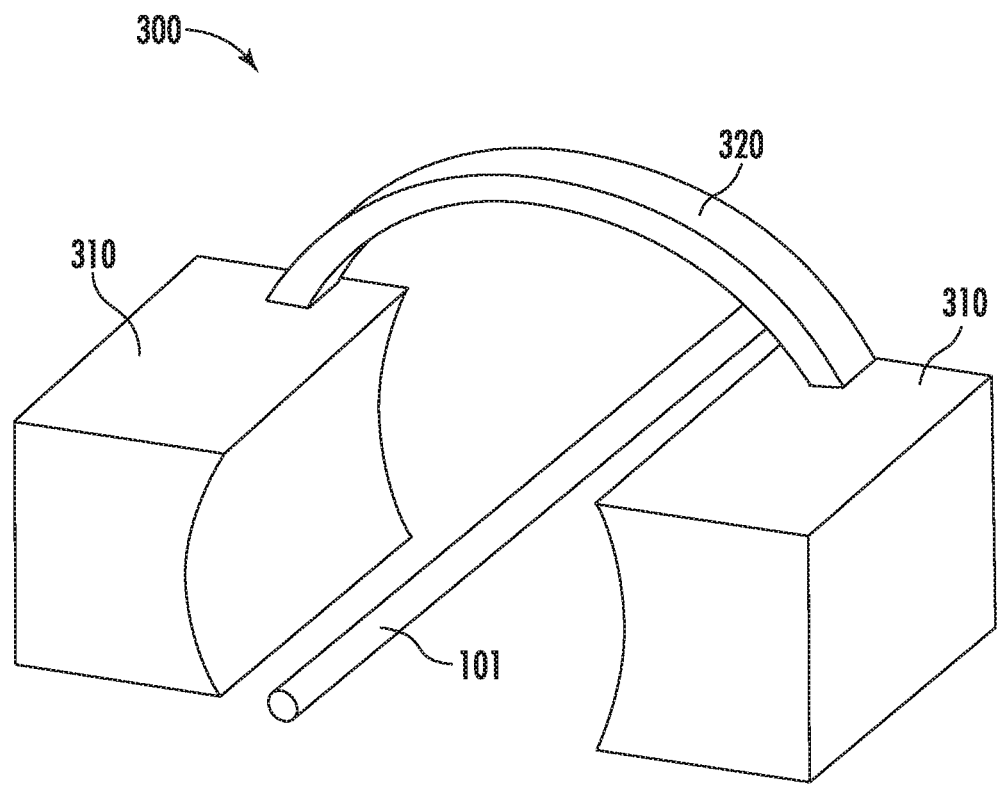
FIG. 10 is a perspective view of an example embodiment of a system including an implantable reconfigurable bone adjustment device and an actuating mechanism.
Figure 11:
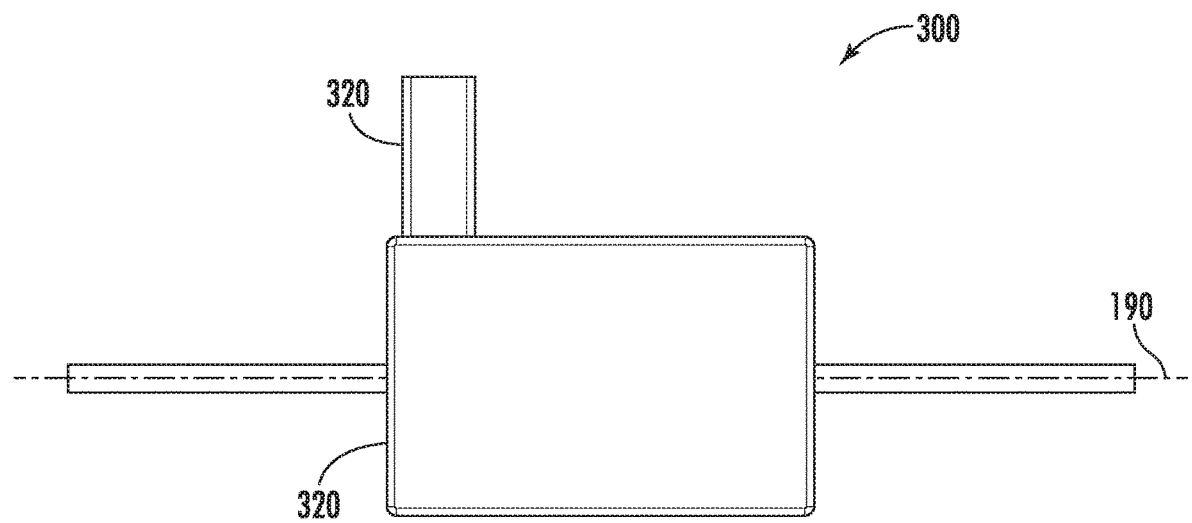
FIG. 11 is a side view of the system shown in FIG. 10.
Figure 12:
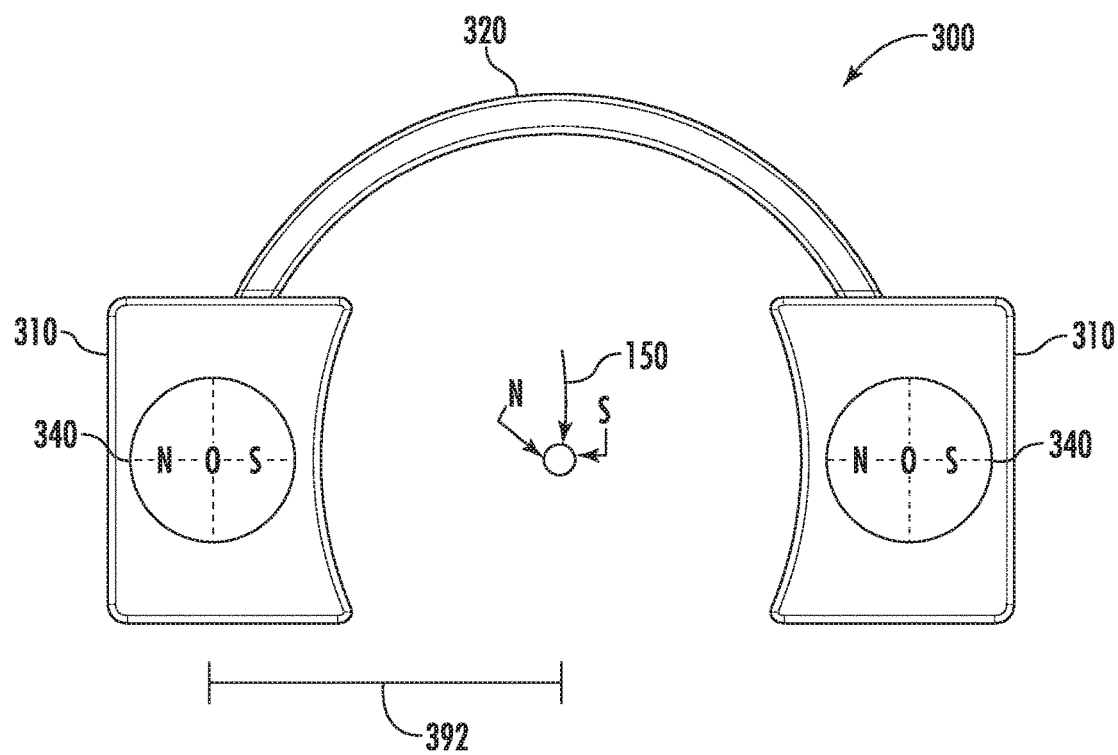
FIG. 12 is an end view of the system shown in FIG. 10, the implantable reconfigurable bone adjustment device illustrated with only the inner magnet shown.

In one embodiment, depicted in FIGS. 10-12, the actuation unit 300 may include a pair of housings 310, an arcuate body 320 connecting the pair of housings 310, and a pair of outer magnets 340 mounted in the pair of housings 310, respectively. In FIGS. 10-12, the actuation unit 300 is illustrated in a position in which it partially surrounds the reconfigurable bone adjustment device such as, for example, the IM limb lengthening nail 101, such that the outer magnets 340 are positioned on opposite sides of the internal magnet 150 of the reconfigurable bone adjustment device. The outer magnets 340 may, for example, be neodymium magnets, although other magnets may be employed as will be apparent to those skilled in the art. With the outer magnets 340 positioned on opposite sides of internal magnet 150, and with each of the outer magnets 340 having an inward-facing side of one polarity aligned with a side of the inner magnet having the opposite polarity, the internal magnet 150 is magnetically coupled to the actuation unit 300. Thus, rotation of the actuation unit 300 about the longitudinal axis 190 of the reconfigurable bone adjustment device results in a torque being applied to the internal magnet 150. As a result of the torque, the internal magnet 150 rotates about the longitudinal axis 190, thereby causing rotation of the threaded rod 170.

In certain embodiments, the arcuate body 320 may include an adjustment device which permits relative movement of the housings 310 in a direction transverse to the longitudinal axis 190 of the reconfigurable bone adjustment device. In such embodiments, the distance 392 (FIG. 12) between the center of internal magnet 150 of the reconfigurable bone adjustment device and the center of outer magnets 340 of the actuation unit 300 may be adjustable in order to accommodate limbs of varying diameters. For example, the housings 310 may be moved further apart from one another in order to accommodate a limb having a larger diameter and may be moved toward one another to increase the strength of the magnetic coupling when the limb has a smaller diameter.

In the illustrated embodiment, the outer magnets 340 are fixedly mounted in the housings 310, and rotation of the internal magnet 150 is achieved by rotating the actuating device 300 about the longitudinal axis 190 of the reconfigurable bone adjustment device. In other embodiments, the outer magnets 340 may be rotatably mounted in the housings 310 of the actuation unit 300. In such embodiments, rotation of the internal magnet 150 may be achieved by rotating the outer magnets while the actuating device 300 remains stationary, as described, for example, in U.S. Pat. No. 8,777, 947 to Zahrly et al, which is hereby incorporated herein by reference in its entirety. Alternatively, another embodiment of an external magnetic actuator is described in PCT Application No.: PCT/US17/68394, filed on Dec. 26, 2017, entitled Actuation System and Method for Orthopedic Implants with a Rotatable Internal Magnet, which is hereby incorporated herein by reference in its entirety.

After implantation of the reconfigurable bone adjustment device in a patient, the external actuation unit 300 may be used at various times, per physician instructions, to non-invasively rotate the internal magnet 150 and the threaded rod 170 of the implantable reconfigurable bone adjustment device, as described herein. As will be appreciated, the ability of the actuation unit 300 to rotate the internal magnet 150 and the threaded rod 170 of the implantable reconfigurable bone adjustment device against the resistive forces of the bone callus and soft tissue is determined in part by the strength of the magnetic coupling between the internal magnet 150 of the implantable reconfigurable bone adjustment device and the outer magnets 340 of the external actuation unit 300. For patients with a large limb diameter, the distance 392 between the internal magnet 150 and outer magnets 340 reduces the strength of the magnetic coupling, which limits the amount of torque that can be applied to the threaded rod 170 and internal magnet 150 by the actuation unit 300. The ability of actuation unit 300 to rotate the threaded rod 170 also depends in part upon the resistive frictional forces internal to the implantable reconfigurable bone adjustment device, such as friction between the engaged threads of the threaded rod 170 and the threaded block 119 in the implantable reconfigurable bone adjustment device.

Orthopedic implants and prosthetics such as implantable reconfigurable bone adjustment devices described herein typically are formed of a biocompatible metal. Medical grade cobalt-chromium (CoCr) alloys such as cobalt-chromium-molybdenum (CoCrMo) and cobalt-chromium-iron (CoCrFe) are among the most suitable metallic biomaterials, particularly for weight-bearing implants. These alloys typically exhibit high mechanical properties, adequate corrosion resistance, and acceptable biocompatibility. In one embodiment, an implantable reconfigurable bone adjustment device according to the disclosure is formed of a cobalt-chromium-iron (CoCrFe) alloy. In another embodiment, the alloy comprises a 40Co-20Cr-16Fe-15Ni-7Mo alloy. It should be appreciated however that the implantable reconfigurable bone adjustment device may be manufactured from any suitable material now known or hereafter developed.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by $\frac{1}{10}$ of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

As will be appreciated from the descriptions herein and the associated Figures, a wide variety of embodiments are contemplated by the present disclosure, examples of which include, without limitation, the following:

The present disclosure provides an implantable reconfigurable bone adjustment device. In one embodiment, the implantable reconfigurable bone adjustment device may be in the form of a length adjustable intramedullary limb lengthening nail comprising an outer body having a distal end opposite a proximal end, the outer body having a notch positioned between the distal end and the proximal end; an inner body having a portion received by the outer body; a threaded shaft coupled to the outer body to rotate relative thereto; an inner magnet received by the outer body and coupled to the threaded shaft for rotation therewith; and a threaded block positioned in the notch and coupled to the outer body, the threaded block having internal threads, the threaded shaft passing through the threaded block and threadedly engaging with the internal threads.

According to some embodiments, the outer body includes a distal end portion that spans between the distal end and the notch.

According to some embodiments, the notch has an elongated shape that includes a center portion that spans between a distal notch end portion and a proximal notch end portion.

According to some embodiments, the distal notch end portion and the proximal notch end portion each have a semi-circular shape, the threaded block includes a distal end opposite a proximal end, wherein the distal end and the proximal end each have a semi-circular shape that is configured to engage the distal notch end portion and the proximal notch end portion, respectively.

According to some embodiments, both the distal end and the proximal end each have a radius that corresponds to a similar radius for distal notch end portion and proximal notch end portion.

According to some embodiments, the inner body includes an end portion and the outer body includes an overlap portion that extends from the distal end towards the proximal end and covers the end portion of the inner body.

In another embodiment, the implantable reconfigurable bone adjustment device may be in the form of a length adjustable intramedullary limb lengthening nail, comprising an outer body having a distal end portion that has a length sized to receive a notch therein, the outer body having an adjacent portion that spans from the distal end portion towards a proximal end, the distal end portion having an outer diameter that is smaller than an outer diameter of the adjacent portion; an inner body having a portion received by the outer body; a threaded shaft coupled to the outer body to rotate relative thereto; an inner magnet received by the outer body and coupled to the threaded shaft for rotation therewith; a threaded block positioned in the notch and coupled to the outer body, the threaded block having internal threads, the threaded shaft passing through the threaded block and threadedly engaging with the internal threads; and a collar sized to fit over the distal end portion and cover the threaded block.

According to some embodiments, the collar has a tubular shape.

According to some embodiments, the collar is attached to the distal end portion by a press-fit configuration.

According to some embodiments, the collar is attached to the distal end portion by a weld.

The present disclosure provides a method of manufacturing an implantable reconfigurable bone adjustment device. In one embodiment, the method of manufacturing the implantable reconfigurable bone adjustment device comprising providing an outer body having a notch in a distal end, the notch being sized to receive a threaded block; positioning a threaded block in the notch of the outer body; depositing a weld at an angle to at least one of the threaded block and the notch to attach the threaded block to the notch, wherein the angle is measured relative to a line perpendicular to the outer body at the location of application of the weld; coupling a threaded shaft to the threaded block; positioning an inner magnet in the outer body; coupling the inner magnet to the threaded shaft for rotation therewith; and assembling an inner body with the outer body wherein the inner body has a portion received by the outer body.

According to some embodiments, the positioning the threaded block in the notch includes positioning a proximal end of the threaded block against an arcuate portion of the notch, and a distal end of the threaded block is substantially flush with a distal end of the outer body.

According to some embodiments, the depositing the weld includes using a laser beam.

According to some embodiments, the depositing the weld includes depositing a first weld at a first angle to a first portion of at least one of the threaded block and the notch and depositing a second weld at a second angle to a second portion of at least of the threaded block and the notch.

According to some embodiments, the first weld is applied at a first energy and the second weld is applied at a second energy, the second energy is different from the first energy.

According to some embodiments, the first portion is an arcuate portion of the notch and the second portion includes a leg portion of the notch.

According to some embodiments, the first angle and the second angle are each between about 10 degrees to about 30 degrees.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments, but that it has the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The foregoing discussion has been presented for purposes of illustration and description and is not intended to limit the disclosure to the embodiments disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments or configurations. Moreover, the following claims are hereby incorporated into this Detailed Description by this reference, with each claim standing on its own as a separate embodiment of the present disclosure.

It should be understood that while the use of words such as preferable, preferably, preferred or more preferred utilized in the description above indicate that the feature so described may be more desirable, it nonetheless may not be necessary and embodiments lacking the same may be contemplated as within the scope of the present disclosure, the scope being defined by the claims that follow. As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The phrases "at least one", "one or more", and "and/or", as used herein, are open-ended expressions that are both conjunctive and disjunctive in operation. The terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. All rotational references describe relative movement between the various elements. Identification references (e.g., primary, secondary, first, second, third, fourth, etc.) are not intended to connote importance or priority but are used to distinguish one feature from another. The drawings are for purposes of illustration only and the dimensions, positions, order and relative to sizes reflected in the drawings attached hereto may vary.

The invention claimed is:

1. An implantable reconfigurable bone adjustment device movable between a retracted state and an extended state, the bone adjustment device comprising:
   a first member configured for attachment to a first bone fragment, the first member including a distal end, a proximal end, and a notch located between the distal end and the proximal end;
   a second member configured for attachment to a second bone fragment, the second member including an elongated slot;
   a drive mechanism configured to move the second member relative to the first member;
   a threaded block fixedly coupled to the first member, the threaded block positioned within the elongated slot formed in the second member and at least a portion of the threaded block being positioned in the notch formed in the first member; and
   a threaded rod having a proximal end operatively coupled to the drive mechanism, an intermediate portion threadably coupled to the threaded block, and a distal end operatively coupled to the second member so that rotation of the drive mechanism rotates the threaded rod and moves the second member relative to the first member;
   wherein:
      the threaded block includes a proximal end and a distal end, the proximal end including an arcuate shape;
      the notch includes a proximal end and a distal end, the proximal end of the notch including a corresponding arcuate shape configured to receive the proximal end of the threaded block; and
      the threaded block is coupled to the first member by a weld positioned along a junction between the threaded block and the notch formed in the first member.

2. The bone adjustment device of claim 1, wherein the proximal end of the threaded block includes a radius and the proximal end of the notch includes a corresponding radius to receive the proximal end of the threaded block.

3. The bone adjustment device of claim 1, wherein the distal end of the threaded block is substantially flush with the distal end of the first member.

4. The bone adjustment device of claim 1, wherein the weld is applied by a laser beam that is positioned at an angle relative to the threaded block and the first member, the angle being between about 10 degrees to about 35 degrees.

5. The bone adjustment device of claim 1, wherein the weld includes depositing a first weld at a first angle to a first portion of the junction and depositing a second weld at a second angle to a second portion of the junction.

6. The bone adjustment device of claim 5, wherein the first weld is applied at a first energy and the second weld is applied at a second energy, the second energy is different from the first energy.

7. The bone adjustment device of claim 5, wherein the first portion is the arcuate proximal end of the notch and the second portion includes a leg portion of the notch.

8. The bone adjustment device of claim 1, wherein the threaded block is welded to the first member by one of varying a weld angle and an energy level of a laser beam during welding.

9. The bone adjustment device of claim 8, wherein a first weld applied along the arcuate shape proximal end of the threaded block and the notch includes a first energy and a first angle, a second weld applied along straight portions of the threaded block and the notch include a second energy and a second angle.

10. The bone adjustment device of claim 9, wherein the second energy level and the second angle are greater than the first energy level and the first angle.

11. The bone adjustment device of claim 1, wherein the distal end of the notch is positioned a distance away from the distal end of the first member.

12. The bone adjustment device of claim 1, wherein the distal end of the notch includes a semi-circular shape for contacting a corresponding semi-circular shape formed on the distal end of the threaded block.

13. The bone adjustment device of claim 1, wherein:
   the first member is an outer body; and
   the second member is an inner body having a distal end and a proximal end;
   a portion of the proximal end of the inner body is received within the outer body so that an overlap portion is formed between the distal end of the outer body and the proximal end of the inner body when the bone adjustment device is in the extended state.

14. The bone adjustment device of claim 13, wherein the portion of the proximal end of the inner body extends from an end of the elongated slot formed in the inner body to the proximal end of the inner body.

15. The bone adjustment device of claim 1, wherein each of the proximal end and the distal end of the notch includes a semi-circular arcuate shape.

16. The bone adjustment device of claim 15, wherein each of the proximal end and the distal end of the threaded block includes a semi-circular arcuate shape for contacting the semi-circular arcuate shape of the proximal and distal ends of the notch.

* * * * *